United States Patent
Bedard et al.

[19]

[11] Patent Number: 6,077,075
[45] Date of Patent: Jun. 20, 2000

[54] DENTAL APPLIANCE AND PROCESS

[76] Inventors: John Arthur Bedard, 11882 Della La., Garden Grove, Calif. 92840; Martin Van Nedderman, 5522 Serene Dr., Huntington Beach, Calif. 92649; Douglas Brian Murphy, 3730 Lee Rd., Mound, Minn. 55364

[21] Appl. No.: 09/227,185

[22] Filed: Jan. 9, 1999

[51] Int. Cl.⁷ .................................................. A61C 13/00
[52] U.S. Cl. .............................. 433/167; 433/213; 264/18
[58] Field of Search ..................................... 433/167, 213, 433/214, 60, 212.1, 222.1, 207, 206, 223, 171; 264/18, 16, 17, 19

[56] References Cited

U.S. PATENT DOCUMENTS

| | | | |
|---|---|---|---|
| 3,727,309 | 4/1973 | Huey | 433/171 |
| 3,839,796 | 10/1974 | Hazar | 433/171 |
| 4,432,730 | 2/1984 | Gettleman et al. | 433/171 |
| 4,654,006 | 3/1987 | Kusano et al. | 433/171 |
| 4,681,543 | 7/1987 | Monroy | 433/167 |
| 4,846,682 | 7/1989 | Ootsubo | 433/167 |
| 5,711,668 | 1/1998 | Huestis | 433/167 |
| 5,939,211 | 8/1999 | Mormann | 433/167 |

*Primary Examiner*—Gene Mancene
*Assistant Examiner*—Pedro Philogene
*Attorney, Agent, or Firm*—Robert A. Elwell

[57] ABSTRACT

A dental appliance and a process for making a dental appliance by forming a laminated vinyl base of closed cell materials using a thermal forming technique and subsequently forming a polymerized overlay resin layer to bond artificial teeth to the base and provide a visible surface for the appliance. The resulting laminated appliance is slightly flexible but the flexibility may be increased by increasing its temperature and thereby facilitate installation over or removal from undercut dental tissues in a patient. The thermal formed intermediate is employed in a "try-in" when temporarily waxed and temporarily fitted with artificial teeth. The intermediate portion of the "try-in" eventually becomes incorporated in the dental appliance. The blanks may be furnished as an array, with flexibility information to assist in selection of an appropriate blank from the array.

17 Claims, 6 Drawing Sheets

DENTAL APPLIANCE AND PROCESS

BACKGROUND

The present invention relates to a dental appliance and a process for making a dental appliance and, in particular, relates to a laminated flexible dental appliance and a process for making a laminated flexible dental appliance.

For many years the dental industry has produced rigid dental appliances, such as dentures, and attempted to achieve a comfortable yet snug fit of the appliances in patients' mouths. Conventional rigid dental appliances do not address day to day changes of oral tissues. For a typical wearer, this shortcoming results in minor but daily irritation and discomfort.

Desired fit and comfort have often been elusive and far too many dental appliances undesirably shift while being worn. This shifting is uncomfortable and disconcerting to patients. In extreme cases, poorly fitting dental appliances may cause ulcers in a patient's mouth. The problem is particularly serious in patients whose dental tissues (especially the gums) include an undercut region.

An undercut region of the gum generally fails to interact with and support a typical rigid dental appliance. This is due to the rigid design of typical dental appliances, which are normally constructed of acrylic. More specifically, because typical dental appliances are rigid, they can not be installed over a patient's gums and still curve inward to fit snuggly against the undercut region of the gum. In use, particularly when biting or chewing, the typical rigid dental appliance sits atop the undercut gum and tends to rock back and forth upon the rounded extreme edge of the gum, with its skirt moving into and out of the undercut region. The rigid opposite opposing skirt also follows the rocking action, whether or not the opposite gum surface has an undercut. Such rocking action is an irritation to the patient and potentially detrimental to the patient's gum tissue and bone adjacent the undercut region.

An additional challenge in dental appliances is to provide dental appliances which are comfortable to a patient. Two prior art approaches to attempt to improve comfort are to improve the fit of the dental appliance and to provide a soft liner. Alternative approaches have been to prepare dental appliances with hinges or to prepare flexible dental appliances employing nylon. While flexible nylon dental appliances might appear to be a promising solution, nylon flexible dental appliances are difficult or even impossible to repair and adjust. The nylon appliances are typically limited to about 1.5 to 2 mm in thickness because thicker nylon appliances are often excessively stiff or even rigid. This in turn means that nylon appliances fail to address the problems of filling in or compensating for destroyed or missing gum tissues, a condition often encountered in patients who have lost a few millimeters to several centimeters of bone and gum tissue to oral cancer surgery. Additionally, instead of rocking on the gum, the flexible nature of the prior art flexible dental appliances undesirably allowed the attached artificial teeth to flex more than desired by most patients. Other prior art attempts at preparing "soft" dental appliances have also been unacceptable due to insufficient strength or durability.

Silicone soft liners have also been tried as a means of improving comfort and fit for dental appliances. However, silicone soft liners are characterized by unacceptable low durability and difficulty in preparation and processing. Silicone soft liners are also porous. Porosity is undesirable because it tends to support micro-organisms, such as bacterial or fungal growths, which in turn generate undesirable tastes and odors as well as additional health challenges for the patient. Soft liners used against acrylic dental appliances are compressible and must rely solely upon the acrylic appliance for strength. If the acrylic appliance portion is too thin, the acrylic will crack when the soft layer is compressed. Typically, the acrylic portion needs to be 3 mm or more in thickness to avoid cracking. Hinges between separate acrylic portions have even been employed to attempt to address these problems. Additionally, the soft liners presently available to the industry do not bond directly to the acrylic, further complicating production and durability problems.

Patients would appreciate a comfortable dental appliance which is strong and durable, installs easily, fits well once installed by closely fitting against any undercut regions, and yet holds artificial teeth firmly in a preselected position relative to the patient's gums. The present invention includes a dental appliance and a process for preparing a dental appliance which addresses these challenges. The materials employed are closed cell materials to discourage micro-organism growth.

SUMMARY OF THE INVENTION

The present invention, in a first embodiment, is a process for preparing a dental appliance, such as a denture or a partial prosthetic device. The process includes steps of providing a cast, which reflects the regions to be contacted by the appliance. Undercut regions may be present in the patient and preferably are retained in the cast. In the process a laminate blank, with a soft layer and a hard, strengthening layer, is also provided. The blank is heated so that it is moldable, and then molded into contact with the study cast. The molded laminate is trimmed to form a try in base plate. A temporary wax layer, bearing artificial teeth, is formed on the try in base plate. The try in base plate, with wax layer and artificial teeth, is tested for fit and comfort in the patient's mouth. The wax layer is subsequently removed and a polymerized overlay layer is substituted therefore. The overlay layer bonds the artificial teeth to the appliance. In this process, any undercut regions of the patient which are retained in the study cast are reflected in the appliance resulting from the process.

In prior art processes, a "try in base plate" (also sometimes termed a "wax base" or a "bite block") is formed, used to design and work toward a better fit of the subsequent appliance, then discarded. This new process is more conservative of materials and more efficient since the try in of this new process need not be discarded.

Preferably, the laminate blank used in the process is characterized by increased flexibility when heated to a temperature which is tolerable to the body, for example roughly 20° F., but possibly even 30° F. for some patients, above body temperature. If so, then the dental appliance which results from the above mentioned process will be suitable for two other embodiments of the present invention. Those processes involve installation and removal of a dental appliance. In the process for installing a dental appliance, the process includes the steps of providing a dental appliance with such characteristics, heating the dental appliance immediately prior to installation, and installing the heated dental appliance. In the process for removing an installed dental appliance, the process includes the steps of providing an installed dental appliance having such characteristics, heating the installed dental appliance to a tolerable temperature immediately prior to removal; and removing the heated dental appliance. In both processes, the heat softens or increases the flexibility of the appliance temporarily so that it can elastically expand over the gum tissue and then return a shape matching the patient's tissues including any undercut regions.

The present invention, in another embodiment, is a laminated dental appliance including a layer of flexible strengthening material. The layer of flexible strengthening material in the laminated dental appliance can be in contact with dental tissues or, preferably, be separated from dental tissue by another layer, most preferably a soft layer. The flexible strengthening material layer is capable of being pressure formed or vacuum formed, when heated, to adapt to the shape of a dental model. Additional efficiency in the process of preparing the appliance is also made available when the flexible strengthening is used as a baseplate for bite registrations and/or "tooth try-ins." When used in laminated dental appliances to supply strength to other flexible layers, the flexible strengthening material layer reduces or limits excessive flexing of the softer resin layer to reduce fatigue failure of the resin layer. Additionally, the flexible strengthening layer reduces tearing and separation in the softer layer. The flexible strengthening layer, due to its action as a reinforcement, allows layers to be present which would more easily tear or break if present alone. Preferably, the flexible strengthening layer is formed of closed cell thermal plastic material. Preferably, the flexible strengthening layer has a thickness of from about 0.6 millimeters to about 1.2 millimeters.

The present invention, in another embodiment, is a dental appliance formed from a laminate having a flexible strengthening layer laminated to a soft material layer. In this embodiment, the soft material layer may be arranged for contact with a patient's dental tissues. The laminate may be formed or shaped, for example, by heating to soften and then exposing to either vacuum or pressure, to adapt to a dental model. The laminate can also be employed during production as a baseplate for bite registrations and/or "tooth try-ins" to facilitate efficiency in the preparation process. The laminate approach also provides improved control of final soft layer thickness by controlling the thickness of the original layer of the laminate blank. The stiffness or flexibility of such a dental appliance is temperature dependent, as well as thickness dependent, such that the dental appliance may be heated to a body tolerable temperature to facilitate installation or removal from undercut regions on a patient's dental tissues. Moreover, the reinforcement of a soft layer or layers by the flexible strengthening layer allows softer material layers, ultimately destined to be placed in contact with a patient's gums, to be fabricated and used in the laminate. Such softer materials could not be effectively used alone to form an unlaminated dental appliance because of their inadequate tear strength. The strengthening layer also inhibits crack propagation in the overlay resin as well as absorbing and dispersing the bending forces applied to the appliance.

The inventors recognize that the laminate of the present invention dental appliance could alternatively include multiple thinner layers of strengthening material(s) which together form a strengthening layer equivalent; or multiple thinner layers of soft material(s) which together form a soft material layer equivalent; or groups of multiple thinner layers with each group working together to form a strengthening layer equivalent and a soft layer equivalent. The underlying concept remains that at least two layers of materials with different property are present in the laminate and working together to contribute to the final dental appliance product, with one layer proving flexible strength and the other layer providing a soft surface.

In yet another embodiment, the invention is a dental appliance which adapts to contact undercut regions in a patient's mouth. The dental appliance may be softened before insertion or removal to ease it over an undercut gum area and into contact with the associated undercut region. The appliance may also optionally be temporarily softened to slightly readapt itself to minor changes that have occurred in the oral tissues, remolding to match and fit with the day to day changes that occur naturally in a patient's mouth. As indicated earlier, the softening may be accomplished by temporary temperature increases above normal body temperature.

In another embodiment, the present invention is an array of dental appliance laminate blanks. The array is made up of a plurality of laminate blanks, where each of the blanks of the plurality are useful for preparation of thermal molded dental appliance intermediate bases which may be subsequently bonded to a resin layer and support artificial teeth thereby forming flexible laminate dental appliances. The array allows a dentist or dental technician to select an appropriate blank from which to form an appliance for a particular patient. This provides simple control over flexibility in the final appliance and therefore easily match the patient's requirements. The blanks in the array vary in flexibility characteristics. This may best be accomplished by varying the thickness of the laminate layers, (but alternatively could be accomplished by using alternative vinyl materials, of differing rigidity, in the strength layer.) The laminates may also be provided in a variety of colors to match the aesthetics of the patient. Preferred colorants are ferric oxide or cadmium-zinc to provide reddish colors. For example, the array would include a laminate with a vinyl, preferably polyvinyl chloride (PVC), strength layer with a thickness of about 0.6 mm and another different vinyl, also preferably a PVC, soft layer with a thickness of about 2.0 mm. More preferably, such a laminate is present in several color variations. The array is accompanied by a selection guide which provides flexibility information concerning blanks of the array and assists the dental professional in appropriate selection from the array.

BRIEF FIGURE DESCRIPTIONS

DETAILED DESCRIPTION

Comprehension of the present invention can be gained through reference to the drawings in conjunction with a through review of the following explanation and examples.

Figure 7:
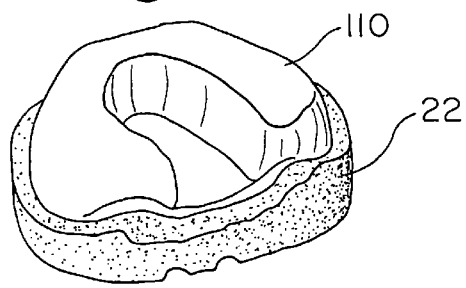
FIG. 7 is a perspective view of a cooled laminate, trimmed to form a base laminate and shown in association with a model to which it was adapted.
Figure 16:
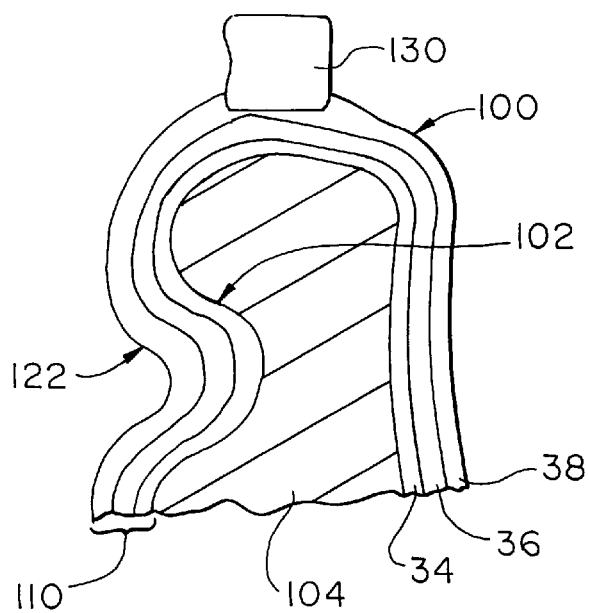
FIG. 16 is a cross-section of the finished dental appliance of FIG. 15 on a patient's undercut gum.

In a first embodiment, the present invention is a process for preparing a dental appliance. The resulting appliance 100 of FIG. 16 has the desirable ability to contact an undercut region 102 of a patient's gum 104. It also has a soft contact surface layer 34 for contacting the patient's gum 104. The flexibility of the appliance can be temporarily altered (softened or made more flexible) by heating to facilitate installation. This temporary heating is especially useful for installing over undercut regions 102, as well as for subsequent uninstalling. There are two major portions of the process, first, preparing a molded thermoplastic, preferably laminated, base 110, shown in FIG. 7, and second, preparing an appliance 100 from the molded laminated base 110, using an overlay resin 112, preferably of vinyl material, however acrylic material might be alternatively employed, and a dental flask 114 by employing a modification of standard flasking procedures. A preferred overlay resin has a copolymer of vinyl chloride and vinyl acetate, methyl methacrylate monomer and di-isobutyl adipate as a plasticizer. Alternatively, an injection system might be substituted for the packing system described subsequently.

Forming a Molded Laminated Base

The initial step in the process is to prepare a working study cast 20 and 22 reflecting the patient's mouth by techniques well known in the dental profession. While not absolutely essential, preparation of a duplicate study cast (i.e master and study casts) is especially recommended in cases where the patient has an undercut region 102 in the gum 104 associated with the patient's oral cavity. On the study cast 20 and 22, the reproduced undercut regions 26, if present, should not be blocked or filled. Rather, any reproduced undercut regions 26 should be retained in the study cast 22 as these regions 26 can be reflected in the final appliance 100. When the patient's undercuts 102 are appropriately reflected as undercut 122 in the final appliance 100, they provide superior retention on the gum 104 of the mouth.

In forming the molded laminated base 110, it is helpful if the height of the study cast 20, 22 is reduced as much as possible. This reduction in height helps to eliminate or minimize localized regions thinning of the laminated base 110 during the subsequent heat molding. (Heat can be supplied, during the process, by ovens, hot water, microwave, or infrared lamps.) Additionally, it is also desirable to reduce the base area of the study cast 20, 22. That is, the smaller the study cast 20, 22, the less thinning and stretching of the laminate sheet 30 and the more effective the application of vacuum or pressure to adapt the laminate sheet 30 to the study cast 20, 22. In preparing appliances 100 for the lower jaw, in particular for patients having long sublingual flanges and undercuts 102, it is essential to remove the lingual portion of the study cast 22.

Once the study cast 20, 22 is prepared and placed in the vacuum molding device 32, the laminate blank 30 should be heated. A suitable vacuum molding device 32 is available from Dental Resources Inc. of Delano, Minn. as the Proform Dual Chamber Vacuum Machine. A suitable laminate blank material 30 has a first, soft layer 34 of PVC vinyl (polyvinyl chloride) and a second, more substantial, hard layer 36 of PVC vinyl. The hard layer 36 reinforces the soft layer 34 and is primarily responsible for control of the flexibility properties in the dental appliance. The preferred hard layer is formed from a polymerized mixture of PVC suspension resin, phthalate plasticizer, epoxy soybean oil, Ca-Zn heat stabilizer and stearic acid. Alternatively, other reinforcement material layers might be present as well. It is the hard layer 36 to which artificial teeth will eventually be bonded. By way of further description, previously known blanks used in preparing devices for reducing the ill effects of nighttime bruxism, available from Dental Resources, Inc. of Delano, Minn. are similar in materials yet distinguishable from the blanks used in the present invention in terms of layer thickness, particularly the thickness of the soft layer, in terms of the provision of an array of thicknesses from which a most appropriate thickness can be selected, in terms of color stability, in an array of color shades, so as to facilitate and maintain cosmetic attractiveness. The further provision of an array from which a selection may be made allows the resulting dental appliance to better fit individual patient needs, desires, and requirements. Specifically, the ability to select from an array of blanks allows the provision of appropriate flex, proper lip support, occlusal opening, facial architecture, and coloring for an individual patient to be incorporated into the resulting dental appliance. Thus, while no two patients are identical, a choice or selection from an array of laminate thicknesses and colors can be used to closely match a wide variety of patient types. The earlier mentioned nighttime bruxism laminate blanks have previously been described in a number of general dental journals and are known to the profession. It should be noted that the array of the present invention and the ability to address flexible laminate based dental appliance requirements are believed to be significant advances in dental appliance technology.

As a guide to selecting a laminate blank for carrying out the present invention, the soft layer 34 should be from about 1 mm thick to about 4 mm thick and have a hardness, as measured on Shore A durometer scale, of from about 60 to about 90 and the hard layer 36 should be from about 0.3 mm thick to about 1.5 mm thick and have a hardness, as measured on Shore D durometer scale of from about 55 to about 85 at room temperature. Preferably, the thickness and hardness of the soft and the hard layers 34, 36 should be about 1.4 mm to about 4.0 mm thick and 70–80 on the Shore A durometer scale and about 0.6 mm to about 1.5 mm thick (most preferably from about 0.6 mm to about 1.2 mm thick) and preferably about 60–70 on the Shore D durometer scale, respectively.

It is preferred that the soft layer 34 be of closed cell material to avoid retention of bacterial, odors and undesirable chemicals and to facilitate hygiene. Preferably, the hard layer 36 is a thermal plastic material which reversibly softens at higher temperature. Preferably this is a vinyl material and most preferably a polyvinyl chloride material. The temperature dependent physical properties of the hard or strength layer 36 is also a significant consideration. That is, in addition to the laminate blank being moldable at high temperatures, i.e. 300–500° F., the resulting dental appliance formed from the laminate blank, when warmed to a tolerable temperature i.e. 120–130° F., will more easily elastically flex to allow relatively comfortable installation on or removal from a patient with an undercut region and then, upon returning to body temperatures, resume its molded shape for contact with the undercut region. (A Universal Test Machine (UTM) and ASTM tests D638 & D790, incorporated herein by reference, may be helpful in comparing and identifying potential, alternative materials for the hard or strength layer according to changes in modulus of elasticity and flexural modulus with temperature and observing the potential material's behavior in response to bending stresses. Addition of elastomeric property modifying agents to promising potential materials might also be employed to generate new materials for both layers.) Similar adaptation of the dental appliance device 100 to structures such as bulbs, flanges, clasps and irregular ridges is also possible. It is further envisioned that additional control of rigidity may be provided by moderate thickening or thinning of the hard layer 36 or by developing ridges or support elements in this layer. It is also possible that additional layers could be present in the laminate blank 30 as long as any such additional layers not interfere with the underlying invention disclosed herein.

Next, heat is applied to the soft vinyl layer side 34 of the laminate blank 30. After 2–3 minutes of heat application, the laminate blank 30 is turned over and additional heat is applied to the hard vinyl layer side 36 of the now warm and softening blank 30. Only about 10 to 20 seconds of additional heating is required on the hard vinyl side layer 36. Care should be exercised to avoid burning or scorching of the material of the laminate blank 30. Generally, the heating process may also be described as raising the temperature of the laminate blank 30 to take into account the thermal index of the hard layer 36 of the laminate blank 30. Preferably, the temperature of the laminate blank, at the initial time of molding, will be in the range of about 375° F. to about 425° F.

After heating the hard layer 36 vinyl side, the heated base material 30 is lowered onto the study cast 20, 22 and suction is applied to pull the softened blank 30 into conformance with the study cast 20, 22. It is often helpful to use additional mechanical force to encourage the softened blank 30 into conformance with the study cast 20, 22. Cold, wet tissue paper or paper toweling 38 may be used to press the base material 30 onto the study cast 20, 22 for improved adaptation. Alternatively or additionally, by placing a knife blade or waxing instrument onto the partially formed, hot base laminate 30 and gently pushing, a tighter fit and conformance in the undercut areas 26 is also encouraged. In the alternative, other pressure molding systems may employed to mold the softened laminate blank to the study cast 20, 22 instead of vacuum molding systems.

Figure 1:
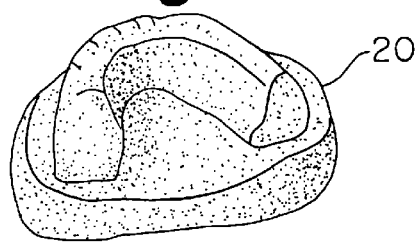
FIG. 1 is a perspective view of a typical model of a patient's upper gum.
Figure 2:
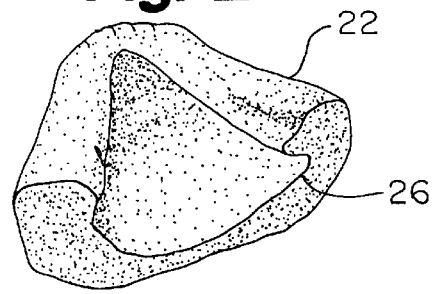
FIG. 2 is a perspective view of another model of a patient's lower gum, including an undercut region.
Figure 3:
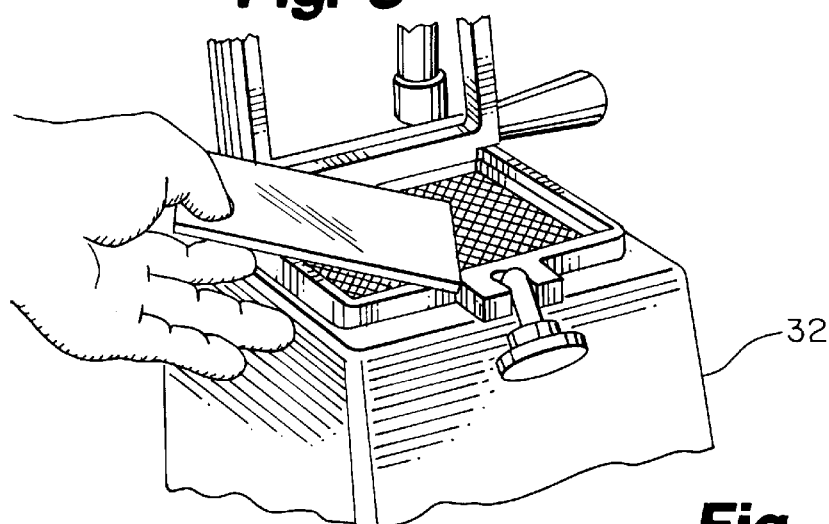
FIG. 3 is a perspective view of a laminate sheet being placed in a vacuum forming machine.
Figure 4:
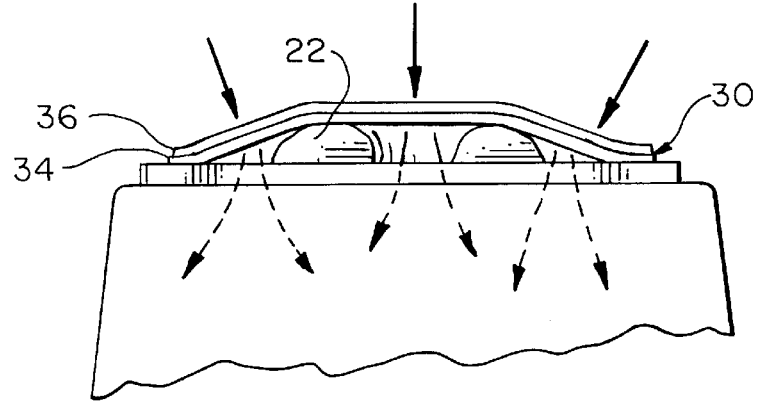
FIG. 4 is a sectional view of a warm laminate being adapted to a model in a vacuum forming machine.
Figure 5:
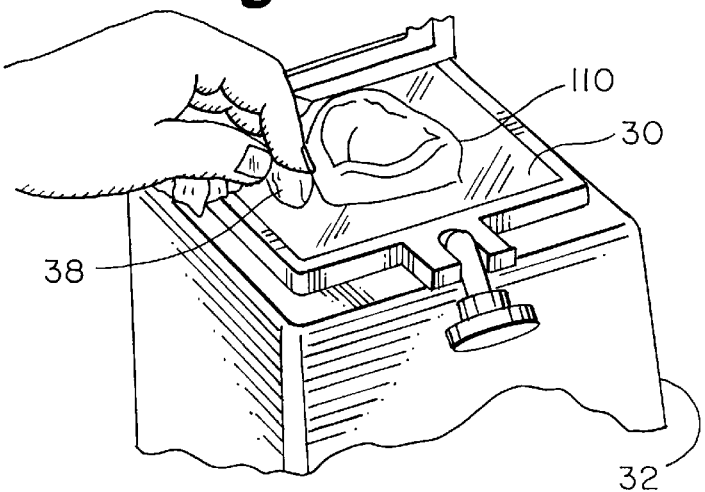
FIG. 5 is a perspective view of a warm laminate being manually pressed against a model.
Figure 6:
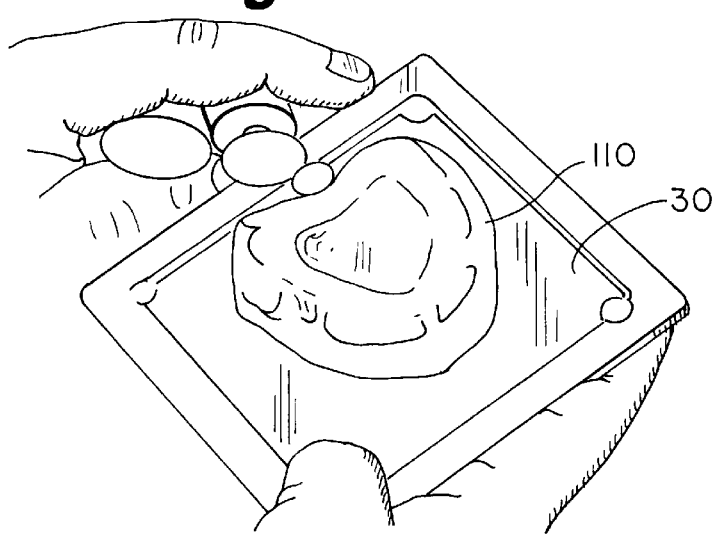
FIG. 6 is a perspective view of the intermediate molded laminate base being trimmed from the laminate blank.

Vacuum molding of the hot base laminate 30 onto the study cast 20, 22 typically requires only about 1 minute. The intermediate molded laminated base 110, including the study cast 20, 22 and molded vinyl laminate 110 is then allowed to cool at least 10 minutes, so that the molded laminate 30 retains the shape of the study cast 20, 22. After cooling, the molded laminate blank 110 with remaining portions of blank sheet 30 is removed from the vacuum device 32 and trimmed to appropriate shape to remove excesses remaining from the initial molding steps as depicted in FIG. 6. The resulting molded base 110 may be finished much as the traditional acrylic bases are finished, however, polishing should not performed upon the molded laminate base 110 at this stage of the process. The molded laminate base 110 is now prepared and ready to be used in preparation of a final dental appliance 100.

The molded laminate base 110 can now be used as a traditional "try in base plate" to assist in designing the dental appliance 100. However, unlike the traditional process, the "try in base plate" of the present invention is conserved and used in the final dental appliance 100.

Preparing the Appliance from the Molded Laminated Base

Figure 8:
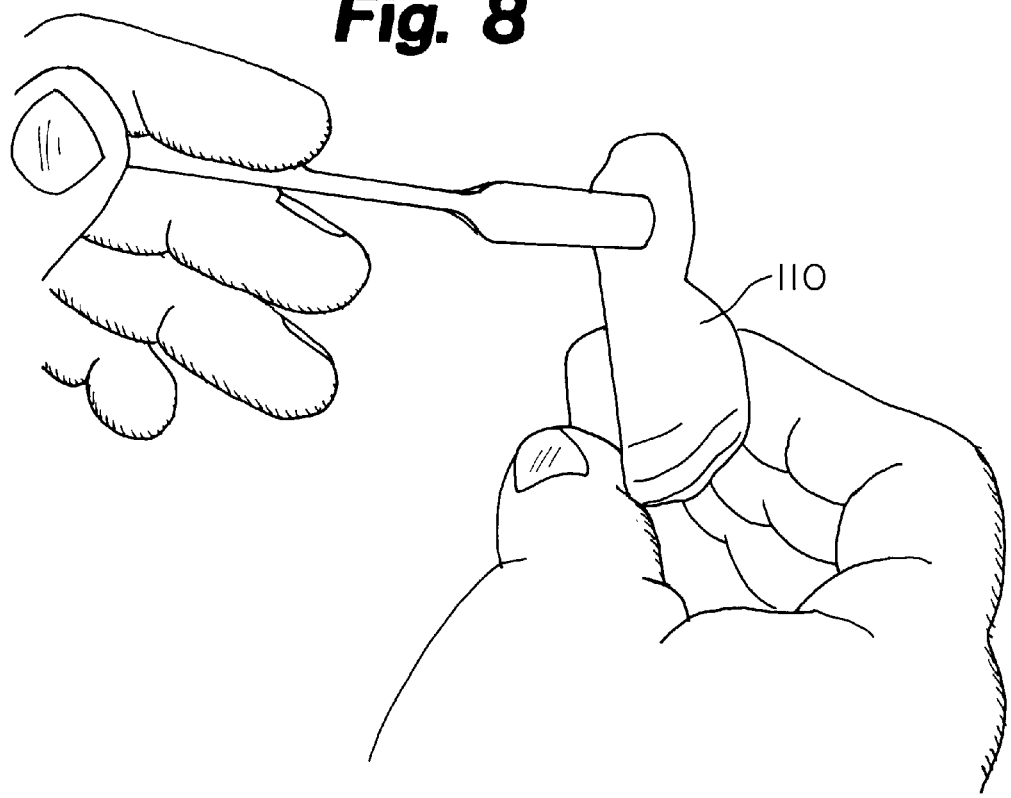
FIG. 8 is a perspective view of a temporary wax covering being applied to the base laminate.
Figure 9:
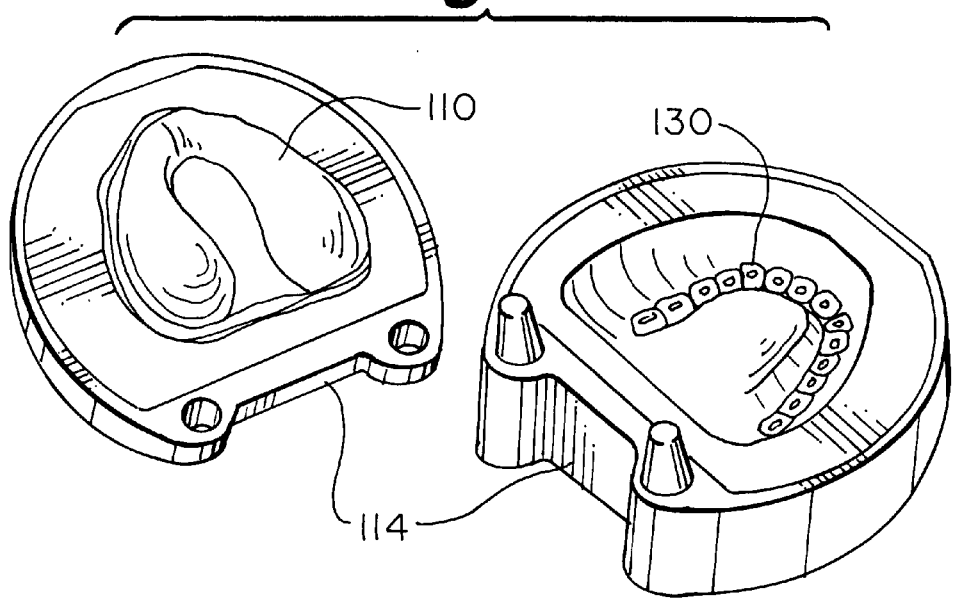
FIG. 9 is a perspective view of both portions of a dental flask with model and wax covered base laminate in one portion and artificial teeth positioned for attachment in the second portion.
Figure 10:
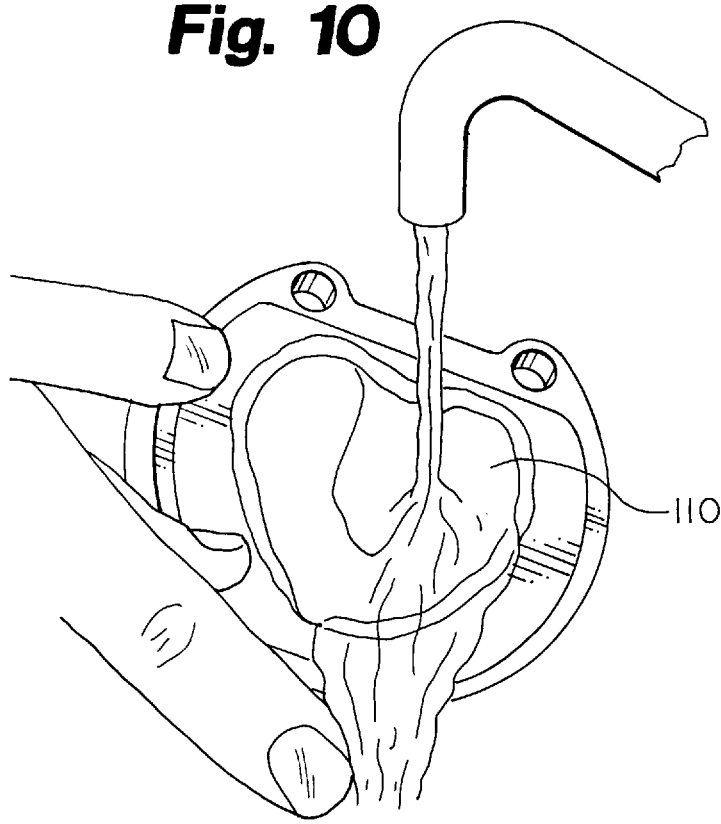
FIG. 10 is a perspective view of of cleaning the base laminate to remove any temporary wax which has not left when liquefied.
Figure 11:
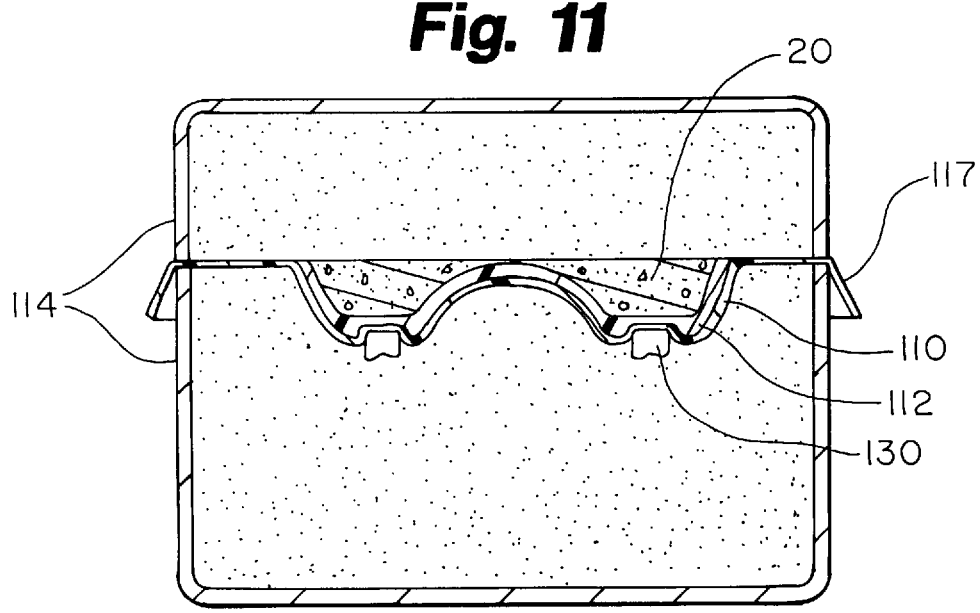
FIG. 11 is a cross-sectional view of the dental flask with model, base laminate, temporary separator, and artificial teeth.
Figure 12:
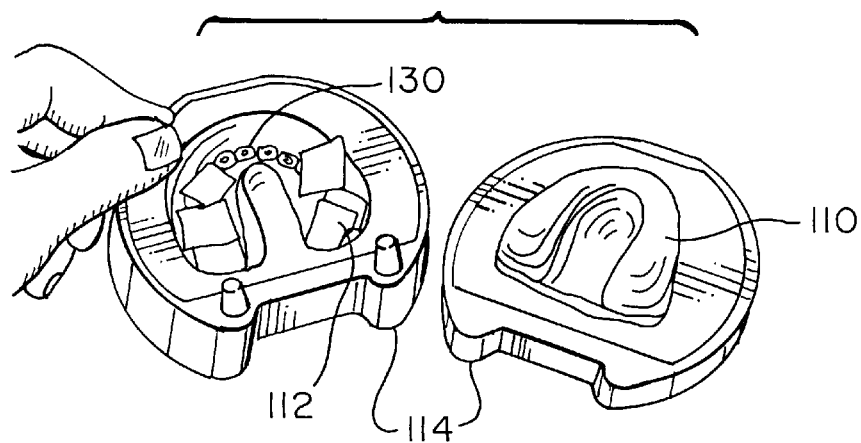
FIG. 12 is a perspective view of the dental flask of FIG. 11, separated and being packed with resin.
Figure 13:
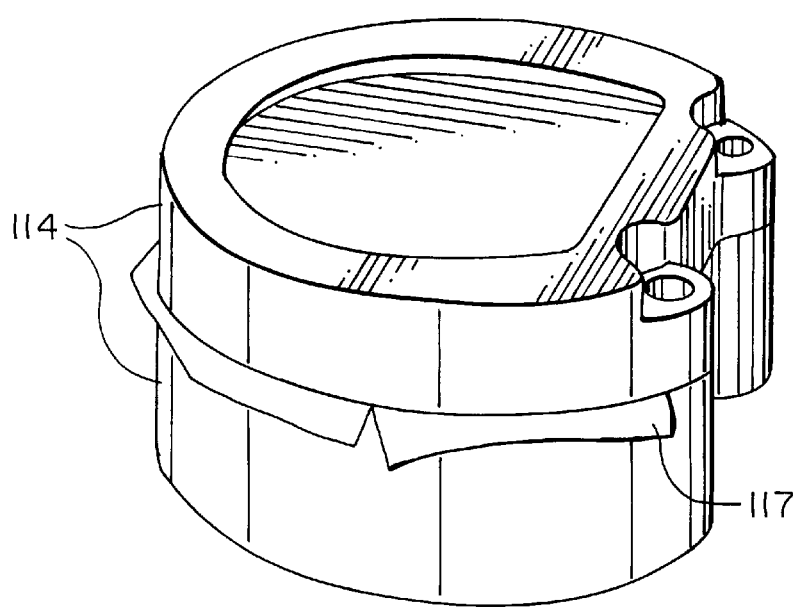
FIG. 13 is a perspective view of the dental flask of FIGS. 11 and 12, assembled with temporary cellophane layer protruding.
Figure 14:
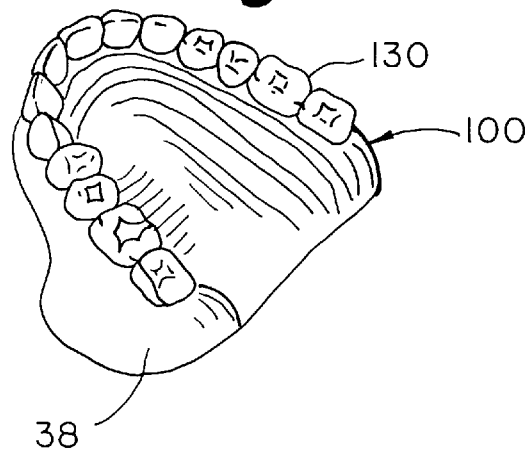
FIG. 14 is a perspective view of the finished dental appliance, showing artificial teeth.
Figure 15:
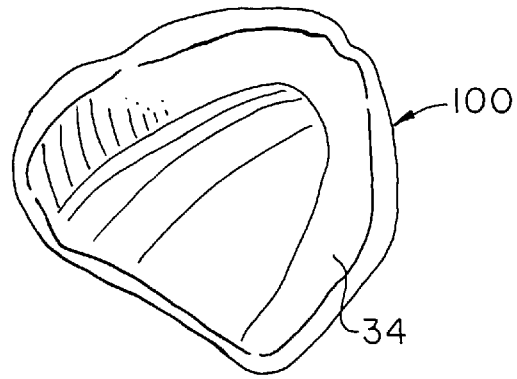
FIG. 15 is another perspective view of the finished dental appliance of FIG. 14, show the gum contacting surface.

Next, a temporary wax coating or layer is added to the laminated base 110 which is being employed as a "try in base plate." This wax coating or layer is similar to other well known dental waxing techniques and depicted in FIG. 8. Considerations such as anatomy, interoccusal space, existing and artificial teeth, are all reflected in the wax added onto the "try in base plate."

During waxing, it is preferred that care should be exercised to cover the entire base laminate 110 with wax before proceeding to the next step. The step of covering with wax, allows one to include any additional anatomical features and to ensure that appropriate depth of color eventually is present in the layer which will replace the wax, thereby closely mimicking the patient's gum tissue appearance. During these steps, care should be exercised to avoid damaging the materials of either layer 34, 36 of the base laminate 110, such as by burning or deforming.

In the next step, a dental flask 114 is prepared by techniques well known in the dental profession. The flask 114 has two portions, one receives the molded laminate base 110 with temporary wax modeling. The molded laminated base 110 including the temporary waxed up model and the teeth 130, positioned in the opposite portion of flask 114, are now "flasked" using conventional methods and materials. Unlike prior art techniques, however, the "try in base plate" is left in the flask 114 and ultimately will be incorporated into the final dental appliance 100. Although optional, additional strength in the final appliance 100 may be obtained by providing mechanical retention of artificial teeth 130, by diatorical holes and other fastener means. However, the present invention does provide adequate chemical bonding of plastic or acrylic artificial teeth 130 to the appliance 100.

The flask 114 is invested, to melt out the wax and leave a space to be filled by a final, third laminate overlay resin layer 38. This is accomplished by heating the flask 114 to melt and liquefy the temporary wax coating or layer. Once liquefied, the vast majority of the wax flows out of the flask 114. Next, to assure complete wax removal, a detergent or detergent wash is applied to the interior space. Optionally, a bonding agent may be applied to the root areas of the artificial teeth at this stage in the process.

Next a temporary layer of cellophane 117 or similar material is placed over the laminate base 110 for trial packing of overlay resin. An excessive volume trial layer of overlay resin 112 is applied to the opposite side of the flask cavity, and the two halves pressed together to bond the overlay resin 112, teeth 130 and laminate base 110 together. When the overlay resin layer 112 has been adjusted to a slight excess volume and preshaped, the cellophane 117 barrier is removed, the flask 114 clamped shut, and the overlay resin 112 polymerized to form overlay layer 38. The polymerization is completed by heating the entire flask 114 in hot water at 165–175° F. for about 1 hour and for another hour at about 200–205° F. or, alternatively, the entire polymerization process is accomplished by heating the entire flask 114 at about 165–175° F. for about 8 hours. (Polymerization can be effected by placing the flask in an oven or hot water. Alternative polymerization means may be substituted, as appropriate to the particular overlay layer materials being employed, but might include microwave or light curing as well for some overlay materials. Alternatively, the overlay layer might be prepared by pouring, press packing, injecting, and cured or polymerized by light or microwave.) After curing, the flask 114 is allowed to cool, for example in cold water, for about 20 minutes. The flask 114 is opened and the nearly finished dental appliance 100 removed. A final polishing of the device 100, using a buffing wheel with light pressure and a small amount of water is recommended.

In installation of the dental appliance 100 of this invention, flexibility can be temporarily increased by moderate warming of the appliance. By way of example, the appliance 100 may be made more flexible by placing it in warm water, roughly 20–30° F. warmer than body temperature or as warm as is tolerable to the patient, immediately before installation. Similarly, a patient desiring to remove the dental appliance, may hold hot water in the mouth for a few moments before removal to increase flexibility. The temperature of the hot water which can be tolerated will of course vary somewhat from patient to patient. It is also possible to locally slightly thin the skirt of the appliance in the region of the undercut to further increase flexibility. The increased flexibility in the skirt will be magnified by the temperature related flexibility increase properties.

In another embodiment, the present invention is an array of dental appliance laminate blanks. The array is made up of a plurality of laminate blanks, where each of the blanks of the plurality are useful for preparation of thermal molded dental appliance intermediate bases which may be subsequently bonded to a resin layer and support artificial teeth thereby forming flexible laminate dental appliances. The array allows a dentist or dental technician to select an appropriate blank from which to form an appliance for a particular patient. This provides simple control over flexibility or elasticity in the final appliance and therefore easily match the patient's requirements. The blanks in the array vary in flexibility characteristics. This may best be accomplished by varying the thickness of the laminate layers. The laminates may also be provided in a variety of colors to match the aesthetics of the patient. For example, the array would include a laminate with a vinyl, preferably PVC, strength layer with a thickness of about 0.6 mm and a vinyl, preferably PVC, soft layer with a thickness of about 2.0 mm. Other less flexible members of the array might have strength layers with thicknesses of about 0.7 mm; 0.8 mm and 0.9 mm. More preferably, such a laminate is present in several color variations. The array is preferably accompanied by a selection guide or instructions which provides flexibility information concerning blanks of the array and assists the dental professional in appropriate selection from the array.

Because numerous modifications may be made of this invention without departing from the spirit thereof, the scope of the invention is not to be limited to the single embodiment illustrated and described. Rather, the scope of the invention is to be determined by appended claims and their equivalents.

What is claimed is:

1. A process for preparing a dental appliance, the process comprising the steps of:

providing a study cast, the study cast having a surface shape closely resembling a selected portion of a patient's mouth and gingivital tissue to be contacted by the dental appliance;

providing a blank laminate, the laminate having a soft vinyl layer and a harder vinyl base layer;

heating the blank laminate to soften the blank laminate to a moldable condition;

molding the heated laminate over the study cast with the soft vinyl layer contacting the surface portion of the study cast surface closely resembling the selected portion of the patient's mouth and gingivital tissue, so as to conform to the selected portion of the patient's mouth and gingivital tissue;

trimming the molded laminate to form a try in base plate;

forming a temporary wax layer bearing artificial teeth on the temperature softenable base layer of the try in base plate;

testing the try in base plate and wax layer in the patient's mouth; and removing the wax layer and substituting therefore a polymerized overlay layer to form a new surface layer bonding artificial teeth.

2. The process of claim 1 and wherein the study cast includes undercut regions.

3. The process of claim 2 and wherein the undercut regions of the study cast are reflected in the dental appliance.

4. The process of claim 3 and further comprising the steps of:

heating the dental appliance to a temperature which is tolerable to the patient so as to temporarily increase flexibility of the dental appliance; and installing the heated, temporarily increased flexibility appliance into the patient's mouth.

5. A process for installing a dental appliance, the process comprising the steps of:

providing a dental appliance having a molded base characterized by increased flexibility when heated to a temperature roughly 20° F. above body temperature;

heating the dental appliance immediately prior to installation; and installing the heated dental appliance.

6. A process for removing an installed dental appliance comprising the steps of:

providing an installed dental appliance having a molded base characterized by increased flexibility when heated to a tolerable temperature above body temperature;

heating the installed dental appliance to the tolerable temperature immediately prior to removal; and removing the heated dental appliance.

7. A laminated dental appliance comprising:

a first layer for contact with gum tissue, the first layer having a first hardness;

a second layer for strengthening the first layer and the appliance, the second layer laminated to the first layer and having a second hardness greater than the first hardness;

a third layer laminated to the second layer, opposite the first layer; and artificial teeth bonded to the third layer.

8. The dental appliance of claim 7 and wherein the second layer is characterized by a first flexibility at body temperature and a second increased flexibility at a temperature above body temperature and wherein the second temperature is tolerable to a patient.

9. The dental appliance of claim 7 and wherein the first and second layers are vinyl polymers.

10. The dental appliance of claim 7 and wherein the first layer is a closed cell material.

11. The dental appliance of claim 7 and wherein the third layer has a coloring similar to the patient's gum color.

12. An array of dental appliance laminate blanks, the array consisting of a plurality of laminate blanks, each of the blanks of the plurality useful for preparation of thermal molded dental appliance intermediate bases which may be subsequently bonded to a resin layer and support artificial teeth thereby forming flexible laminate dental appliances.

13. The array of claim 12 and wherein the blanks of the array vary in flexibility characteristics.

14. The array of claim 12 and wherein the blanks of the array vary in laminate thicknesses.

15. The array of claim 12 and wherein the blanks of the array vary in color.

16. The array of claim 12 and wherein one of the blanks of the array has a vinyl strength layer with a thickness of about 0.6 mm and a vinyl soft layer with a thickness of about 2.0 mm.

17. The array of claim 12 and further comprising a selection guide, the selection guide providing flexibility information concerning blanks of the array.

* * * * *